United States Patent [19]

Mann et al.

[11] Patent Number: 4,751,321

[45] Date of Patent: Jun. 14, 1988

[54] PRODUCTION OF PHOSPHINITES AND PHOSPHONITES

[75] Inventors: Jonathan Mann, Thirsk; Gordon Shaw, Guisborough, both of England

[73] Assignee: Imperial Chemical Industries PLC, London, England

[21] Appl. No.: 10,494

[22] Filed: Feb. 3, 1987

[30] Foreign Application Priority Data

Feb. 11, 1986 [GB] United Kingdom ............... 8603276
Apr. 11, 1986 [GB] United Kingdom ............... 8608803

[51] Int. Cl.$^4$ ............................. C07F 9/46; C07F 9/48
[52] U.S. Cl. ................................................... 558/134
[58] Field of Search ........................... 558/134; 568/17

[56] References Cited

U.S. PATENT DOCUMENTS 3,316,333 4/1967 Hechenbleikner .................. 558/117
4,212,831 7/1980 Nakayama et al. ................. 568/17
4,556,740 12/1985 Hansen et al. ...................... 568/17

FOREIGN PATENT DOCUMENTS 3521770 9/1986 Fed. Rep. of Germany .
99494 8/1981 Japan .................................... 568/17

OTHER PUBLICATIONS

Chemical Abstracts, vol. 96, No. 5, p. 695 (Feb. 1, 1982) Abstract No. 35536p.
Chemical Abstracts, vol. 54, No. 20, (Oct. 25 1960) Abstract No. 20822d, e.

*Primary Examiner*—Anton H. Sutto
*Attorney, Agent, or Firm*—Cushman, Darby & Cushman

[57] ABSTRACT

Phosphinites or phosphonites are produced by reacting potassium or sodium aryls with compounds of formula ROPClX in which X is an R'O, Cl or aryl group, R and R' being alkyl or cycloalkyl groups at a temperature of at most 10° C.

9 Claims, No Drawings

PRODUCTION OF PHOSPHINITES AND PHOSPHONITES

This invention relates to the production of phosphinites and phosphonites.

Phosphinites and phosphonites have valuable catalytic properties for example in the dimerisation of acrylonitrile. Known processes for producing them include the reaction of a Grignard reagent with an appropriately substituted phosphorus halide in a suitable solvent. Such processes are difficult to carry out and involve the use of magnesium and often of bromine. It is desirable however to use cheaper materials.

It is also known from Chemical Abstracts Vol 96 No 35536p to produce triaryl phosphines by reacting aryl halophosphines with alkali metal aryls at temperatures of 20° to 30°.

This invention comprises producing a phosphinite or phosphonite by reacting a potassium and/or more preferably sodium aryl of formula KAr or NaAR with a phosphorus compound of formula ROPClX in which X is Ar', R'O or Cl in which R and R' are alkyl or cycloalkyl groups preferably having 1 to 20 and more preferably 2 to 10 carbon atoms, for example an isopropyl or cyclohexyl group at a temperature of below 10° C. and preferably −30° to 10° C. and more preferably −20° to 5° C. The Group X is preferably RO or Cl.

It is desirable to operate at temperatures below 10° C. because at higher temperatures the RO group of the phosphorous compound tends to be replaced by an Ar group producing a tertiary phosphine. The production of such tertiary phospines not only represents a loss of yield; they are detrimental to the performance of the desired products as catalysts in the dimerisation of acrylonitrile and must therefore be removed from the product.

The Ar and Ar' groups are preferably phenyl groups which may be substituted in the 3, 4 or 5 positions by electron donating groups, that is, by groups which tend to donate electrons to the 1 position of the phenyl group. Such substituents may be alkyl or aryl groups, and may be cycloalkyl or aryl groups fused with the phenyl group at two of the 3, 4 or 5 positions. For example, potassium and/or sodium naphthyls or substituted naphthyls may be used. The phenyl group may alternatively be substituted in the 3, 4 or 5 positions by alkoxy, aryloxy, dialkylamino or alkyl or aryl thio substituents. The substituents should not themselves be capable of reacting with potassium and/or sodium. Suitably such substituents together comprise a total of at most 10 and preferably at most 6 carbon atoms.

The process is exothermic and is suitably carried out in the presence of an inert diluent, for example a hydrocarbon diluent which may be a paraffinic or aromatic diluent by adding one reactant (preferably the potassium and/or sodium aryl) slowly with cooling to the other in the substantial absence of oxygen and water. The pressure is preferably at most 10 bars absolute. Preferably at completion a stoichiometric amount or slight excess of the potassium and/or sodium aryl has been introduced, for example up to a 5% excess. The diluent is suitably present in at least an amount by weight of 3 and preferably at least 5 for example 5 to 50 times the weight of the reactants.

If the potassium and/or sodium aryl is produced by reacting the corresponding aryl chloride with the potassium and/or sodium it may be convenient to include a dispersing agent for the potassium and/or sodium at that stage. It is not in general necessary to remove this before carrying out the process of this invention, and the crude potassium and/or sodium aryl may normally be used therefore without further treatment.

Suitably the potassium and/or sodium aryl may be produced as follows. First the potassium and/or sodium is dispersed in an inert liquid medium for example a hydrocarbon medium. The dispersion may be carried out with the aid of ultrasonic vibration but is readily carried out by agitation of the molten potassium and/or sodium with the inert liquid medium. It is preferred to use a dispersing aid for example carbon black or an aluminum or alkali metal salt of a carboxylic acid having 10 to 25 carbon atoms. The dispersion suitably comprises 5 to 50% and preferably 10 to 20% of sodium and/or potassium by weight. If a dispersing agent is present it may be 0.01 to 1% by weight of the potassium and/or sodium.

Suitable inert liquid media are those which are liquids at the melting point of the sodium and/or potassium at a pressure of 1 to 5 bars absolute. If desired a lower boiling medium may be used under higher pressure.

Preferably, at least 90% of the potassium and/or sodium particles are smaller than 100 and preferably smaller than 50 $\mu$m in diameter.

The sodium and/or potassium may then be reacted with a bromo or preferably chloroaromatic compound corresponding to the desired aryl by adding it slowly to the dispersion at a temperture of 10° to 40° C. and preferably 15° to 30° C. with agitation, preferably under the influence of ultrasonic vibration. Preferably addition is stopped leaving a slight excess for example of 0.1 to 5% excess of the sodium and/or potassium. If desired the chloroaromatic compound may be added as a solution in an inert solvent.

The crude product of the invention is suitably washed with cold water under neutral or alkaline conditions (preferably below 10° C.) and the organic layer distilled to remove any diluent and to separate the pure product.

When washing with water it is preferred that an organic base be present as we have found that even if the crude product equilibrates to neutrality or alkalinity during washing a transient concentration of HCl may arise. Suitable bases include amines, for example $C_1$ to $C_6$ alkylamines, aniline, diaminobenzenes and pyridine. If the base is present during the reaction of the potassium and/or sodium aryl with the phosphorus compound it should be an amine which contains no reactive hydrogen atoms, for example pyridine or preferably a tertiary alkyl and/or aryl amine, suitably having 3 to 20 carbon atoms in total in its molecule.

EXAMPLE 1

Sodium (60 g, 2.608 Moles) was melted in refluxing petroleum ether (100° to 120° C. boiling range, 400 ml) containing aluminium stearate (0.06 g) as a dispersing agent. Reflux was maintained whilst the suspension was agitated for 10 minutes using a homogenising mixer at 4,000 rpm approximately. The agitation was then stopped and the dispersion allowed to cool to ambient temperature. The resulting dispersion had >90% of its particles below 50 $\mu$m in diameter. This and all subsequent operations was carried out under an inert $N_2$ atmosphere.

To this dispersion was added, with mechanical and ultrasonic agitation, p-chlorotoluene (162.8 g, 1.28

Moles) in petroleum ether (100° to 120° C. boiling range, 100 ml). The addition was dropwise, at such a rate as to maintain a reaction temperature of 20° to 30° C. with the reactor immersed in an ice-water bath. The addition was complete after 1½ hours and the products were stirred without cooling for a further 1 hour.

The resulting crude, black suspension containing the tolylsodium reagent was transferred over a period of two hours into a second reactor containing isopropylphosphorodichloridite (isoPrOPCl$_2$), (93.2 g, 0.58 moles) in petroleum ether (100° to 120° C. boiling range, 300 ml) with mechanical stirring. The reaction temperature was maintained between −10° and 0° C. by immersing the reactor in a cooling bath. Addition of the tolylsodium was continued until it was just in excess over the isopropylphosphorodichloridite. This was determined by withdrawing an aliquot and adding to it an equal volume of demineralised water. The pH of the water layer was then measured. A pH>7.0 is indicative of an excess of tolylsodium, whereas a pH<7.0 is indicative of an excess of isopropylphosphorodichloridite.

Demineralised water (500 ml) which had previously been deoxygenated by purging with nitrogen was added to the reaction mixture at 0° C. with stirring. The resulting lighter hydrocarbon phase was collected and the solvent was distilled off. This left a crude oil which contained isopropyl, bis-[4-methylphenyl] phosphinite as the major product (80% by molar proportion). By-products included tritolylphosphine and diisopropyl, (4-methylphenyl) phosphonite. The oil was distilled to give pure isopropyl, bis-[4-methylphenyl] phosphinite (110 g, 70% yield based on isopropylphosphorodichloridite, boiling point 120° C. at 0.1 mm Hg).

On repetition of the above preparation on larger scale it was found that the ultrasonic agitation was unnecessary. Instead of the demineralised water used above to dissolve inorganic materials to promote phase separation dilute NaOH solution (0.01% w/w in water) can be used with advantage.

EXAMPLE 2

A sodium dispersion was made as in Example 1 using sodium (30 g, 1.304 moles) and aluminium stearate (0.18 g, 0.6% mass of sodium) in petroleum ether (250 ml, 100° to 200° C. boiling range). This and all subsequent operations were carried out under an inert N$_2$ atmosphere.

To this dispersion was added, with mechanical stirring, p-chloro-o-xylene (89.99 g, 0.64 moles). The addition was dropwise, at such a rate to maintain a reaction temperature of 30° to 40° C. with the reactor immersed in an ice-water bath. The reaction mixture was thinned with petroleum ether (50 ml 100° to 120° C. boiling range) during the reaction the addition was complete in 1 hour and the products were stirred without cooling for a further 1 hour. The mixture was again thinned with petroleum ether (50 ml, 100° to 120° C. boiling range).

The resulting crude, black suspension containing the xylylsodium reagent was transferred over a period of 1¼ hours into a second reactor containing isopropylphosphorodichlorodite (isoPrOPCl$_2$), (46.69 g, 0.29 moles) in petroleum ether (175 ml, 100° to 120° C. boiling range) with mechanical stirring. The reaction temperature was maintained between −10° and 0° C. by immersing the reactor in a cooling bath. Addition of the xylylsodium was continued until it was just in excess over the isopropylphosphorodichlorodite. This was determined by withdrawing an aliquot and adding it to an equal volume of demineralised water. The pH of the water layer was then measured. A pH>7.0 is indicative or an excess of xyxlylsodium, whereas a pH<7.0 is indicative of an excess of isopropylphosphorodichlorodite. When the pH reading was pH>7.0 triethylamine (3 ml) was added and the mixture stirred for 5 minutes.

0.01 m sodium hydoxide (250 ml) which has previously been deoxygenated by purging with nitrogen was added to the reaction mixture at 0° C. with stirring. The resulting lighter hydrocarbon phase was collected and the solvent distilled off. This left a crude oil which contained isopropyl, bis-[3,4-dimethyphenyl] phosphinite as the major product (79.5% by molar proportion). By-products included trixylylphosphine and diisopropyl, [3,4-dimethylphenyl] phosphonite. The oil was distilled to give pure>98%) isopropyl, bis-[3,4-dimethyllphenyl] phosphinite (60.5 g, 69.5% yield based on isopropylphosphorodichlorodite. Boiling point 150° C. at 0.03 mmHg).

EXAMPLE 3

A suspension of tolylsodium was prepared from sodium dispersion (60 g, 2.608 Moles) and p-chlorotoluene (162.8 g, 1.28 Moles) as described in Example 1. This and all subsequent operations were carried out under an inert N$_2$ atmosphere.

The tolylsodium suspension was transferred over a period of two hours into a second reactor containing cyclohexylphos-phorodichloridite (116.58 g, 0.58 Moles) and triethylamine (5 g, 0.05 Moles) in petroleum ether (100° to 120° C. boiling range, 300 ml) with mechanical stirring. The reaction temperature was maintained between −10° and 0° C. by immersing the reactor in a cooling bath. Addition of the tolylsodium was continued until it was just in excess over the cyclohexylphosphorodichloridite. This was determined by pH testing as described in Examples 1 and 2.

0.01 Molar Sodium hydroxide solution [500 ml] which had been deoxygenated by purging with N$_2$ was added to the reaction mixture at 0° C. with stirring. The resulting lighter hydrocarbon phase was collected and the solvent was distilled off. This left a crude, yellow oil which contained cyclohexyl, bis-[4-methylpheny] phosphinite as the major product (71.3% by molar proportion). By-products included tritolylphosphine and dicyclohexyl, (4-methylphenyl) phosphonite. The oil was distilled to give pure (>98%) cyclohexyl, bis-[4-methylphenyl]phosphinite (120 g, 66.3% yield based on cyclohexylphosphorodichloridite Boiling point 180° C. at 0.05 mm Hg).

EXAMPLE 4

Example 1 was repeated except that triethylamine (4 g, 0.04 moles) was present in the second reactor together with the isopropyl phosphorodichloridite in petroleum ether.

Analysis of the crude oil production (which was produced in substantially the same quantity) showed on four successive similar experiments contents of isopropyl (4-metyl phenyl) phosphonite in the range 85 to 90% by weight, representing a substantial improvement on the 80% previously obtained. Thus the yield of the desired product is improved and its purification is facilitated.

What is claimed:

1. A process which comprises producing a phosphinite or phosphonite by reacting a potassium or sodium aryl of formula KAr or NaAr with a phosphorus compound of formula ROPClX in which X is Ar', R'O or Cl in which R and R' are alkyl or cycloalkyl groups and Ar and Ar' are aryl groups, at a temperature of −30° C. to 10° C.

2. A process as claimed in claim 1 in which the groups R and R' have 2 to 10 carbon atoms, and in which the group X is RO or Cl.

3. A process as claimed in claim 1 or 2 in which the temperature is −20° to 5° C.

4. A process as claimed in claim 1 in which the Ar and Ar' groups are phenyl groups optionally substituted in the 3, 4 and/or 5 positions by electron donating groups.

5. A process as claimed in claim 4 in which the electron donating groups are alkyl groups together comprising at most 10 carbon atoms.

6. A process according to claim 1 which is carried out in the presence of an inert diluent by adding one reactant slowly to the other with cooling in the substantial absence of oxygen and water.

7. A process as claimed in claim 1 in which a slight excess of the sodium and/or potassium aryl is introduced.

8. A process as claimed in claim 1 in which the crude product of the reaction is washed with water at a temperature of at most 10° C. under neutral or alkaline conditions and the organic layer distilled to remove any diluent and to separate the pure product.

9. A process as claimed in claim 8 in which an organic base is present during the washing process.

* * * * *